US00PP09865P

United States Patent [19]

Ralli et al.

[11] Patent Number: Plant 9,865

[45] Date of Patent: Apr. 22, 1997

[54] TABLE GRAPE NAMED 'RALLI SEEDLESS'

[75] Inventors: Giuseppe Ralli; Iolanda Ralli; John Ralli; Joseph Ralli, all of Victoria, Australia

[73] Assignee: G & I Ralli & Sons, Victoria, Australia

[21] Appl. No.: 520,375

[22] Filed: Aug. 29, 1995

[51] Int. Cl.[6] ..... A01H 5/00

[52] U.S. Cl. ..... Plt./47.1

[58] Field of Search ..... Plt./47.1, 47.2, Plt./47.3

[56] References Cited

U.S. PATENT DOCUMENTS

P.P. 3,106 4/1972 Garabedian ..... Plt./47.3
P.P. 8,463 11/1993 Bianco ..... Plt./47.1

*Primary Examiner*—James R. Feyrer
*Attorney, Agent, or Firm*—Lyon & Lyon

[57] ABSTRACT

A new and distinct variety of grapevine producing very low acid red seedless table quality grapes which are obtuse-ovate shaped and medium to large in size.

1 Drawing Sheet

BACKGROUND

This invention relates to a new and distinct variety of the *Vitis vinifera* species and is a sport of the Menindee Seedless variety. The varietal will be identified commercially as Ralli Seedless. The Menindee Seedless is known as the "Sugraone" in the United States, and was patented under U.S. Plant Pat. No. 3,106. The Menindee Seedless is also known commercially as the "Superior Seedless".

The new variety is the result of a single bud mutation grown in Mildura, Victoria, Australia on property owned by the inventors. The new variety has been brought to fruiting and asexually reproduced from cuttings taken from the mutation at the same location. The variety has been propagated by vegetative propagation through four generations. When grown to maturity and bearing, such asexual reproductions ran true to the originally discovered sport in all respects.

SUMMARY OF THE INVENTION

The Ralli Seedless variety may be distinguished from its parent Menindee Seedless and other cultivars by a number of characteristics. It can be distinguished from the Menindee Seedless variety, which it most closely resembles, by among other things, its skin and leaf colors, bud shape, and upper leaf shape. The Ralli Seedless skin color is cardinal red (R.H.S. 822/3) as opposed to the green-yellow color of the Menindee Seedless. Both the Ralli Seedless and Menindee Seedless leaves are a medium green, but the Ralli Seedless leaves develop a red tinge that intensifies as they mature. The Ralli Seedless has a pointed bud shape and open upper leaf shape whereas the Menindee Seedless has a slightly pointed bud shape and slightly overlapping upper leaf sinus shape.

The Ralli Seedless is distinguishable from other cultivars by its very low acid fruit. The Ralli Seedless is palatable at 15° Brix and by the time it gains full color reaches 18° Brix. As compared with the Sugraone, tests conducted on a sample of 100 berries randomly selected show that, at the same stage of development, the Ralli Seedless had 16 brix sugar and 0.53 grams/100 ml acid, while the Sugraone has 14 brix sugar and 0.47 grams/100 ml acid. The new variety also matures about 12 to 15 days ahead of the Thompson Seedless also known as 'Sultana'.

BRIEF DESCRIPTION OF THE DRAWINGS

The accompanying photographs show typical specimens of the fruit and leaves of the new variety in color as nearly true as it is reasonably possible to make in a color illustration of this character.

DETAILED BOTANICAL DESCRIPTION OF THE PLANT

Figure 1:
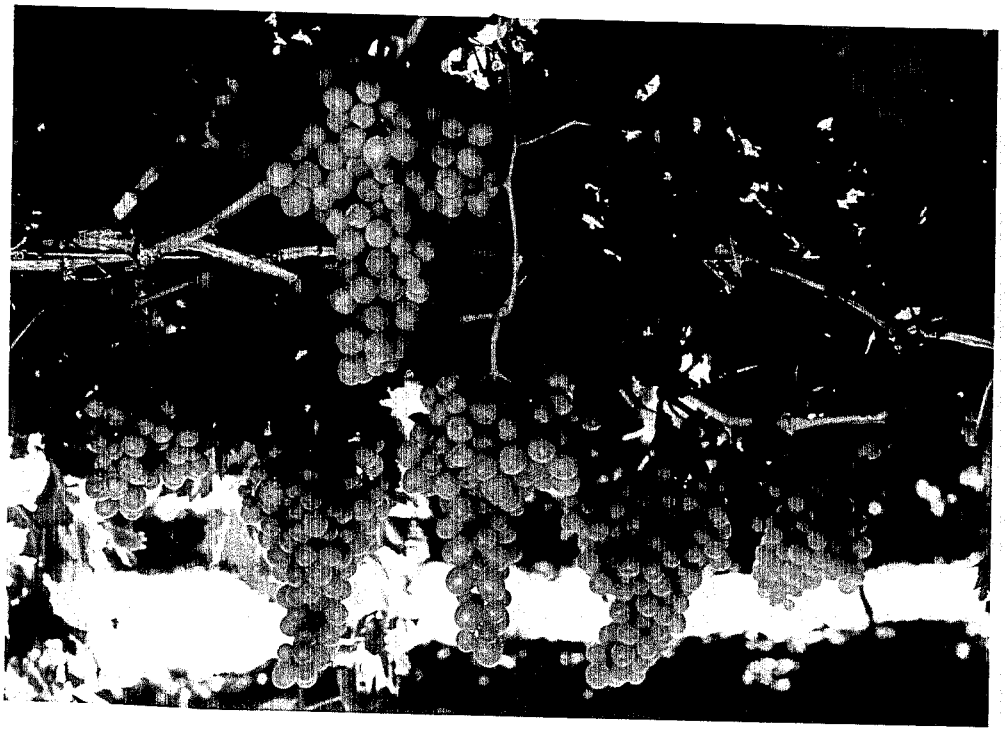
FIG. 1 illustrates a typical cluster of grapes, stem section, and mature leaves of the new Ralli Seedless grapevine.
Figure 2:
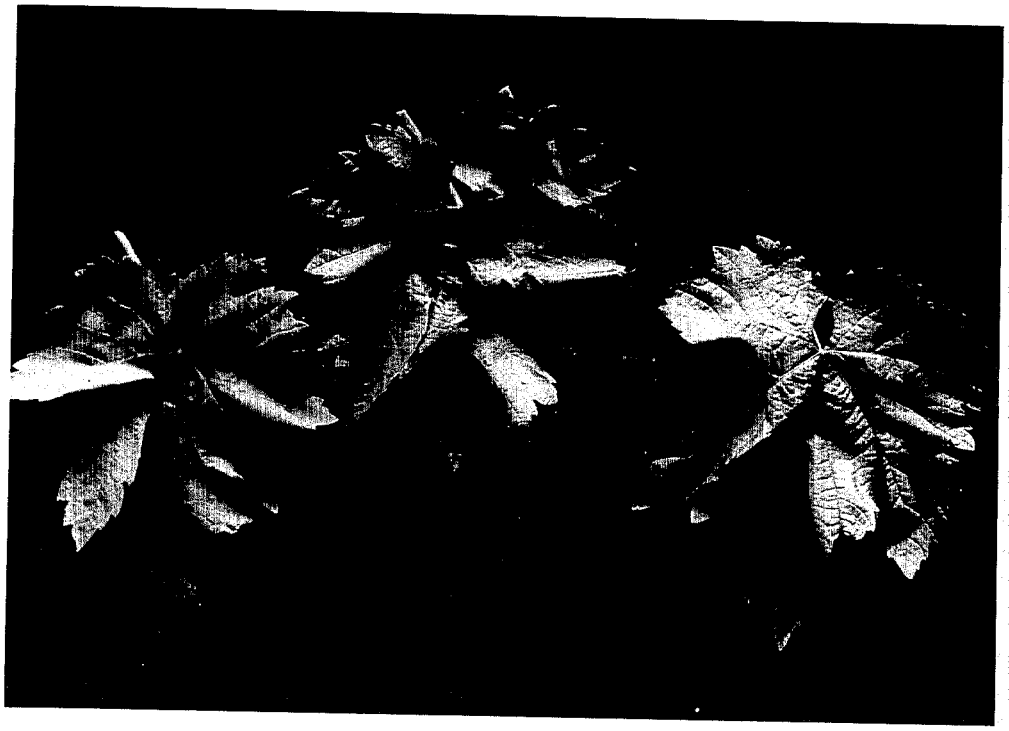
FIG. 2 illustrates the leaves of the Ralli Seedless grapevine.

The following is a detailed description of specimens of the new variety grown at block 598 Cardross, Mildura, Victoria, Australia. Throughout this specification, color names followed by the designation "(R.H.S.)", with a number value following R.H.S., designate values based on The Royal Horticultural Society Colour Chart (R.H.S. Wilson 1938 edition), and refers to plate numbers in the aforementioned color chart. Other color names signify that the name of the color, as used in common speech, is aptly descriptive.

Origin

This variety arose from the spontaneous mutation of "Menindee Seedless" in 1990. The grapevine of the present invention was asexually reproduced by the inventors and the same attributes observed in the parent were found precisely to have been duplicated in the progeny.

Fruit

This fruit is used as a table grape and has very low acidity. It is palatable at 15° Brix and matures 12 to 15 days before the Thompson seedless. Testing in 1993 and 1994 shows that when fruit reaches 15° Brix, the brix to acid ratio is approximately 30:1. When the Ralli Seedless reaches full color it reaches about 18° Brix. The fruit also matures early, around the tenth of January in Mildura, Australia. The time to maturity for the Ralli Seedless is about 72 days as opposed to 68 days for the Menindee Seedless. The cropping duration for the Ralli Seedless is about 30 days as opposed to 14 days for the Menindee Seedless.

The Ralli Seedless stores very well, up to about eight weeks. It also ships extremely well, with very low shatter and no bruising. The Ralli Seedless if comparable to the Thompson Seedless in terms of shipping quality.

Bunches are medium large, about 0.5 to 0.75 kg. The bunches have a loose conical shape, 200 to 250 mm long and 100 to 150 mm wide.

The berries are short elliptic to long elliptic shaped, and of medium to large size, 16 to 20 mm wide, and 20 to 25 mm long. A few small 8 to 10 mm round berries also set and mature. The color is cardinal red (R.H.S. 181-A). The flesh is firm with tough skin. The flesh is also crisp and excellent to eat. The berries contain 2 to 3 rudimentary soft seed trace per berry. These are not noticeable when eating.

Vine

The Ralli Seedless is extremely vigorous, and produces a strong vine. Sprouting occurs in early September, approximately September 1 in Mildura, Australia. The trunk has a large diameter of about 75 mm on three year old vines. The bark is brown, straight grained, and the outer layer is easy to remove.

At verasion, the canes are green with red tinge, especially on the dorsal side. Canes are long, about 2 to 3 meters. Internodes are 75–100 mm. Canes are narrow, 12–15 mm in diameter. Mature canes are light brown and semi-erect.

Flowering of the Ralli Seedless occurs early, around November 4 in Mildura, Australia. This variety has about 0.5 inflorscences per shoot per plant. Six stamens and 1 pistil are produced. The flowers are hermaphroditic with good self compatibility and of intermediate diameter.

Foliage

The Ralli Seedless shoot tips are half open, have no hairs, and have a red tinge. The stem color is pea green (R.H.S. 61/2) with a red tinge. The stems are smooth. The buds are medium, pointed, and a pea green color (R.H.S. 61/2). Generally, the upper surface of a young leaf is Spinach Green (R.H.S. 960 to 960/1) in color while the undersurface of a young leaf is Spinach Green (R.H.S. 960/2) in color. Mature leaves are medium green with a red tinge that increases with maturity. The anthocyanin content of mature leaves is of medium intensity. Both upper and lower leaf surfaces are smooth with no hairs. The color of the Petioles and the color of the veins of the leaves of Ralli Seedless are the same as the color of veins on the leaves of the parent variety, Menindee Seedless.

There are an average of 10 mature leaves above the cluster at the middle of the third shoot. The internode length at maturity varies from about 3.9 to 12.4 cm. The leaves have a large blade length, about 125 to 275 mm long, 125 to 175 mm wide, with convex sides. Petiole sinuses are slightly open to slightly closed. Upper leaf sinuses are open. The leaves are smooth on both sides and the leaf margin is serrated. The leaf blade is pentagonal shaped and the teeth of the leaf margin are convex shaped on both sides. Their color is medium green with a red tinge that increases with maturity. On young leaves the petiole length is approximately 70 to 100 mm. The length of the main vein ranges from about 7.6 to 13.7 cm. The tendrils are around 20.4 to 25.5 cm in length. They are of medium thickness and are discontinuously distributed on the shoot at full flower. Some tendrils produce leaves. The tendrils are yellow green in color.

DNA Profile

DNA profiles of the Ralli Seedless, Menindee Seedless, Sultana and Riber varieties were created using Random Amplification of Polymorphic DNA assays that utilize Polymerase Chain Reaction technology. The absence or presence of bands of DNA were expressed as a similarity matrix indicating a measure of relatedness between varieties. The results were as follows, indicating the Ralli Seedless to be significantly different than the other varieties tested:

Similarity Matrix

| | | | | |
|---|---|---|---|---|
| Ralli | 100% | | | |
| Menindee | 89.8% | 100% | | |
| Sultana | 64.4% | 71.1% | 100% | |
| Riber | 69.4% | 62.7% | 61.0% | 100% |
| | Ralli | Menindee | Sultana | Riber |

What is claimed is:

1. A new and distinct red seedless grape plant known as "Ralli Seedless", substantially as shown and described.

* * * * *